United States Patent [19]

Clark et al.

[11] Patent Number: 4,624,656
[45] Date of Patent: Nov. 25, 1986

[54] HYPERBARIC GAS TREATMENT DEVICE

[75] Inventors: David W. Clark, Fairhaven; George J. Jablonsky, Highlands, both of N.J.

[73] Assignee: Hospitak, Inc., Lindenhurst, N.Y.

[21] Appl. No.: 685,749

[22] Filed: Dec. 24, 1984

Related U.S. Application Data

[63] Continuation-in-part of Ser. No. 516,573, Jul. 25, 1983, abandoned.

[51] Int. Cl.$^4$ .............................................. A61M 1/00
[52] U.S. Cl. ...................................... 604/23; 604/289
[58] Field of Search ..................... 128/200.27, 200.28, 128/206.12, 206.15, 206.17, 206.21, 206.24, 206.28, 207.11, 207.13, 205.26, 202.12, 155, 157, 132 D; 604/23, 289, 304, 305, 389

[56] References Cited

U.S. PATENT DOCUMENTS

| | | | |
|---|---|---|---|
| 2,837,090 | 6/1958 | Bloom et al. | 128/206.24 |
| 3,026,874 | 3/1962 | Stevens | 604/305 |
| 3,137,295 | 6/1964 | Stansfield | 128/206.24 |
| 3,167,070 | 1/1965 | Silverman | 128/206.24 |
| 3,258,011 | 6/1966 | Goodman | 604/289 |
| 4,024,862 | 5/1977 | Collins | 128/132 D |
| 4,122,552 | 10/1978 | Tedford | 604/389 |
| 4,480,638 | 11/1984 | Schmid | 604/23 |

Primary Examiner—Henry J. Recla
Attorney, Agent, or Firm—Eisenman, Allsopp & Strack

[57] ABSTRACT

A hyperbaric gas treatment device applicable to any part of the body for therapeutic topical treating of a skin lesion at the body part. A resilient pad is provided with a central opening therethrough in its thickness direction whose periphery at one major pad surface registers with the periphery of a hole provided through gas-impervious transparent flexible sheet material which encases the pad. The pad casing is hermetically penetrated by a gas inlet fitting arranged to discharge treating gas into the central opening either directly, by extending laterally through the pad to pierce the wall of the opening, or indirectly, by extending between the casing and a peripheral surface portion of the pad so as to communicate with the opening by way of paths between the casing and the pad periphery which link with paths between the casing and at least one of the major pad surfaces. In use, the encased pad is yieldably pressed against the body part with the casing hole periphery circumscribing the lesion, and pure oxygen from a regulated source connected to the inlet fitting enters the central opening of the pad to impinge at hyperbaric pressure upon the lesion and escape to atmosphere past the casing hole periphery in paths it dynamically establishes between the body part and the pad casing. Similarly operative embodiments of the device include those in which the pad casing is omitted, the central opening is only partially through the pad, and a second gas fitting is dedicated to internal pad pressure indication and relief.

20 Claims, 8 Drawing Figures

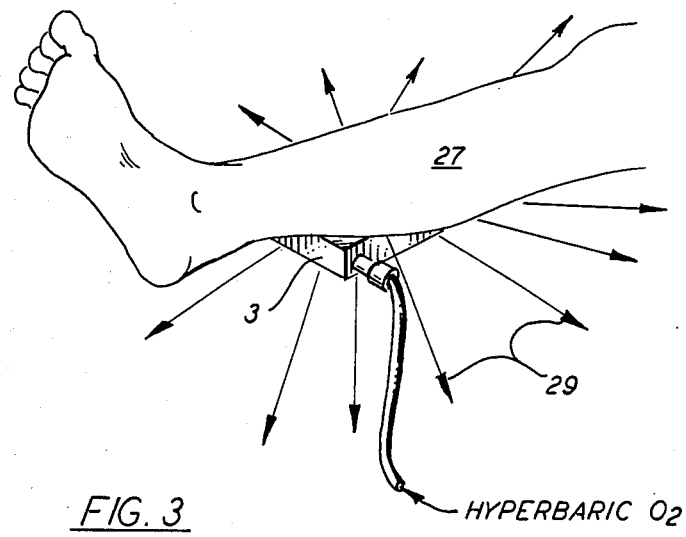
FIG. 3 — HYPERBARIC O2
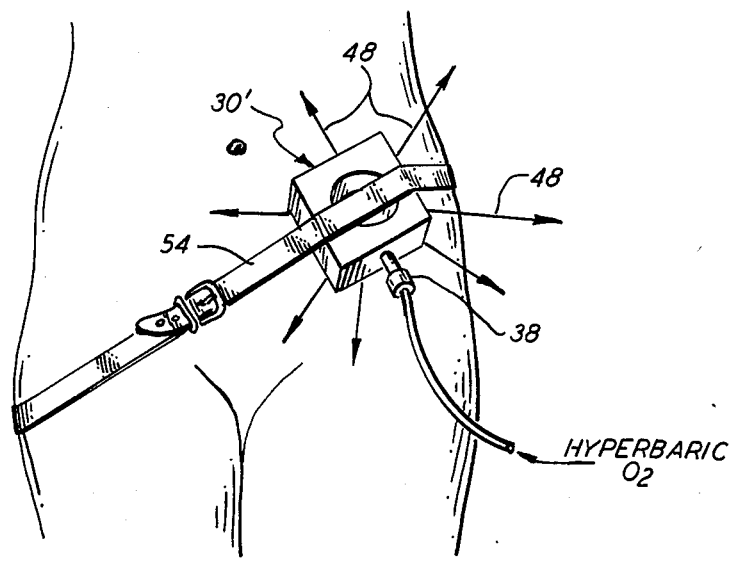
FIG. 4 — HYPERBARIC O2

HYPERBARIC GAS TREATMENT DEVICE

RELATED APPLICATIONS

This application is a continuation-in-part of application Ser. No. 06/516,573, filed July 25, 1983, now abandoned.

BACKGROUND OF THE INVENTION

This invention relates to hyperbaric gas treatment devices and, more particularly, to devices which apply localized hyperbaric oxygen therapy to skin lesions.

The devices heretofore used in therapeutic topical hyperbaric oxygen treatment generally employ a sleeve-like oxygen chamber which receives and encloses a limb having a skin lesion or employ a cup-like oxygen chamber which is applied directly to the skin with its mouth circumscribing the lesion. Apart from its greater applicability to different parts of the body, the cup-like chamber in comparison with the sleeve-like chamber permits less exposure of unafflicted local areas of the patient's skin to pressurized treating gas, whereby its use involves less risk of pressure interference with capillary circulation in such local areas. However, significant risk in respect of such interference still remains as a result of design measures effected to take into account the widespread belief that a gas-tight seal should be provided between the skin and the mouth of the cup-like chamber.

For example, U.S. Pat. No. 4,224,941 granted Sept. 30, 1980 discloses a hyperbaric topical treatment device employing a flaccid oxygen bag which is rendered leak proof by bonding an annulus defining its mouth to a pad, so that a central opening in the pad registers with the mouth, the pad being adhered in gas-tight relation to the skin of the patient with the central opening cupped over the lesion in circumscribing relation. A hyperbaric oxygen atmosphere is then maintained in the bag, and exerts a force on the annulus which combines with the adhesive force between the pad and skin to doubly ensure against leakage from the inflated bag.

Another design measure consonant with the prior art belief that the gas-tight seal should be provided is illustrated in U.S. Pat. No. 4,328,799 granted May 11, 1982. There, a hyperbaric topical treatment device employs a rigid cup-like oxygen chamber which is rendered leak proof by forcefully maintaining a resilient sealing gasket at the mouth of the chamber against the skin of the patient so as to circumscribe the lesion.

The prior art belief has even been respected in designing non-hyperbaric topical treatment devices, as can be seen from U.S. Pat. No. 3,610,238 granted Oct. 8, 1971. There, a porous pad is encased by flexible sheet material adhered only to the opposed major surfaces of the pad so as to leave an annular oxygen channel surrounding the pad periphery, the pad having a central opening which extends through the sheet material at both major pad surfaces. The encased pad is either adhered or taped to the skin of a patient with the central opening mouth at the lower major pad surface cupped over and circumscribing the lesion in gas-tight sealing relation. Pressurized oxygen is fed to the peripheral oxygen channel for passage through the porous pad into the oxygen chamber formed by the central opening where the oxygen passes over the lesion and, being blocked by the gas-tight seal around the lesion, freely escapes from the unobstructed opening at the upper major pad surface, thereby to prevent atmospheric dust from settling on the lesion.

In each of the foregoing prior art disclosures, the design measures taken to provide a gas-tight seal at the lesion-circumscribing mouth of the oxygen chamber will cause pressure to be exerted on the local skin area which may interfere with capillary circulation and which, in view of the tenderness and sensitivity of such area, will at least be a source of unwelcome irritation.

SUMMARY OF THE INVENTION

It is therefore an object of the present invention to improve hyperbaric gas treatment devices of the kind employing a cup-like oxygen chamber which is to be applied directly to the skin with its mouth circumscribing a lesion.

A further object of the present invention is to provide a hyperbaric treatment device of the above-stated kind that can be operatively applied to a skin area without interfering with the capillary circulation in the skin area and without irritating the skin area.

These and other objects are attained by providing, in accordance with the present invention, a hyperbaric gas treatment device comprising a resilient pad having a centrally apertured surface as a major side thereof, means for conducting pressurized treating gas into the central aperture, and means for constraining the pressurized gas flowing into the aperture to escape from the aperture past the aperture perimeter, the apertured surface being yieldably pressable against the skin of a patient to circumscribe the aperture perimeter substantially about a lesion of the skin, and upon conduction of pressurized treating gas into the aperture, to provide gas escape paths between the skin and the apertured surface, in which paths the escaping gas flows from the aperture perimeter to atmosphere to induce a soothing pad vibration transmittable by the apertured surface to the skin.

The central aperture may extend completely through the pad to another major side thereof, in which event the constraining means preferably comprises a casing of gas-impervious flexible sheet material encasing the pad and having a single opening therethrough, the perimeter of which is adjacent the lesion-circumscribing aperture perimeter at the first-mentioned major side of the pad and substantially registered therewith. When the pad is so encased, the conducting means may comprise a gas inlet fitting which penetrates the casing so that its outlet is disposed between the casing and the periphery of the pad to communicate with both ends of the central aperture by way of linking paths defined by the pad periphery and the casing and by each of the two major sides of the pad with the casing. If one should wish the gas inlet fitting to communicate at its outlet with one end only of the central pad aperture, say the aperture end remote from the casing hole, one would adhere the casing region surrounding the casing hole to the adjacent pad surface.

BRIEF DESCRIPTION OF THE DRAWINGS

In order that the invention may be more fully understood, it will now be described with reference to the accompanying drawings, in which:

FIG. 3 is a perspective view illustrating a patient's leg resting on the device shown in FIG. 1 and undergoing treatment by the device while the patient is recumbent on a hospital bed;

FIG. 4 is a perspective view illustrating a modified version of the device shown in FIG. 2 held by a strap against the skin of a patient's abdominal region while applying hyperbaric oxygen thereto;

DESCRIPTION OF THE INVENTION

Figure 1:
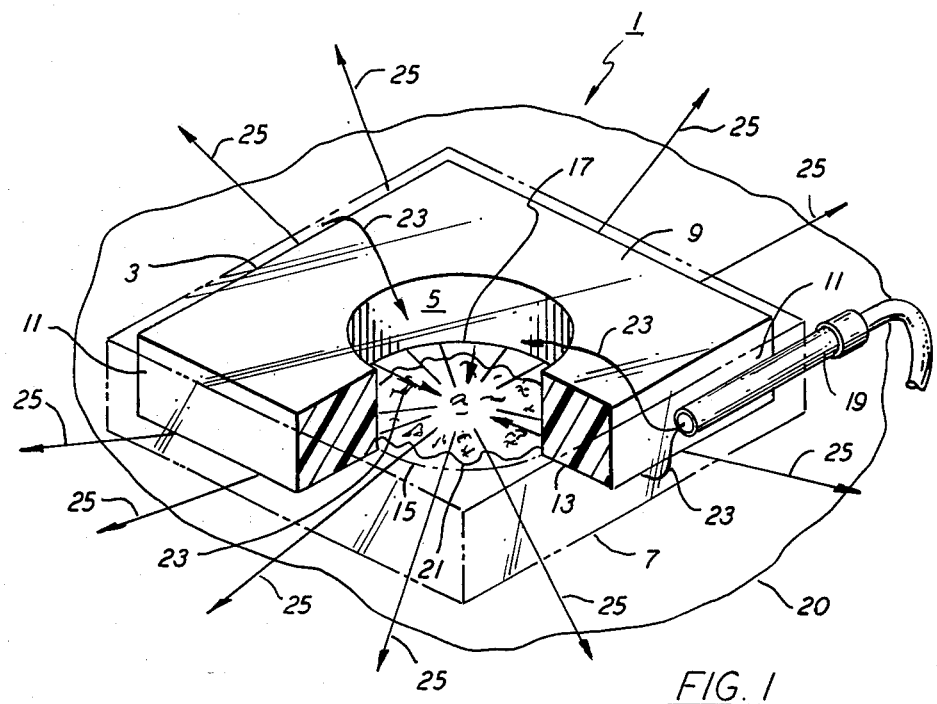
FIG. 1 is an isometric half sectional view of a hyperbaric gas treatment device in accordance with the present invention.

Referring to FIG. 1, a hyperbaric device 1 embodying the present invention is provided with a square resilient pad 3 of soft-foamed plastic material having a central cylindrical aperture 5 therethrough, the pad being encased in a casing 7 of gas-impervious transparent flexible sheet material represented in phantom outline which functions as a soft or pliable gas constraining membrane while affording visibility for the skin lesion.

The four minor surfaces 11 of pad 3, the upper major pad surface 9 and the lower major pad surface 13 are loosely engaged by the respectively adjacent portions of the casing sheet material, but these portions inflate slightly away from pad 3, as generally represented in FIG. 1, when device 1 is operating. In the portion of the casing sheet material adjacent lower major pad surface 13, a circular hole is centrally provided whose perimeter 15 registers with the lower perimeter 17 of aperture 5 so that gas within aperture 5 can escape from device 1 at lower major surface 13. A gas inlet fitting 19 hermetically penetrates casing 7 near a corner of pad 3 and extends a short distance alongside one of minor pad surfaces 11 for supplying device 1 with hyperbaric oxygen from a suitable regulated source (not shown).

In operation, device 1 is positioned on the patient's body 20 so that registered perimeters 15 and 17 of the casing hole and pad aperture 5 circumscribe a skin lesion 21 to be treated. Such positioning is faciliated by the visual access obtained to lesion 21 through the window provided over aperture 5 at upper major surface 9 of pad 3 by the transparent sheet material of casing 7.

Once pad 3 is properly positioned, it is yieldingly held against the patient's body 20, and hyperbaric oxygen is supplied via gas inlet fitting 19 to outwardly distend the casing portions adjacent minor pad surfaces 11, upper major pad surface 9 and at least part of the lower major pad surface 13, thereby to provide linking paths between casing 7 and pad 3 for the hyperbaric oxygen to enter both ends of aperture 5 and impinge at hyperbaric pressure upon lesion 21. The force by which pad 3 is yieldably pressed against the patient's body 20 is one which discourages lateral displacement of the pad, but which allows the lesion-impinging hyperbaric oxygen in aperture 5 to establish escape paths to atmosphere between the patient's body and the encased pad. Such force is therefore insufficient to establish a gas-tight seal around lesion 21 that would tend to interfere with local capillary circulation. In fact, the escape of oxygen made possible by the yieldably pressing nature of such force develops a soothing pad vibration that is imparted to the tender sensitive skin area immediately surrounding the lesion.

As indicated by arrows 23 in FIG. 1, hyperbaric oxygen exits from fitting 19 into both ends of aperture 5 via the spaces its pressure, preferably 22 mm Hg, establishes between casing 7 and pad surfaces 9, 11 and 13. The hyperbaric oxygen in aperture 5 impinges upon lesion 21 and finds an escape route out of device 1 past perimeter 15 of the casing hole and along paths which its pressure establishes between the patient's skin and the skin-contacting portion of casing 7 adjacent pad surface 13. These escape paths are indicated by arrows 25 in FIG. 1.

In order to exert the holding force by which pad 3 is yieldably pressed against body 20 of a patient recumbent on a hospital bed, use may conveniently be made of the height-adjustable table generally associated in overlying relationship with the bed. The recumbency of the patient would be suitably arranged so that the table could be simply lowered to press gently against upper major surface 9 of pad 3 while the pad is properly positioned on the patient's body. Alternatively, pad 3 may be held in proper position on the patient's body by means of straps, strips of tape or like holding elements whose use readily permit the required yieldable pressing action to be achieved. It is even practical in some cases to place pad 3 between the top of the mattress and the body of the recumbent patient so that the pad is held in proper position by a portion of the patient's weight while still being yieldably pressed against the body. Such a case is depicted in FIG. 3 wherein a skin lesion on the calf of the right leg 27 of a patient is undergoing a hyperbaric oxygen treatment applied by pad 3. Arrows 29 indicate the streamers of oxygen which escape to atmosphere via paths between the patient's calf and the portion of pad 3 on which the calf rests.

Reverting to FIG. 1, the soft-foamed plastics material at pad 3 may have an open-cell structure to provide auxiliary paths of communication from fitting 19 to central aperture 5. These auxiliary paths may be converted to principal paths by bonding the flexible sheet material of casing 7 to upper and lower major pad surfaces 9, 13 so that hyperbaric oxygen from fitting 19 can only reach central aperture 5 through the open cells in pad 3. Alternatively, by bonding the casing sheet material only to a single major pad surface, one can route hyperbaric oxygen into aperture 5 at the opposite major pad surface as well as through the open cells in pad 3. Thus, an adhesive bond between lower major pad surface 13 and the adjacent casing sheet material would block the entry of hyperbaric oxygen into aperture 5 at lower pad surface 13 and cause hyperbaric oxygen to be routed into aperture 5 at upper pad surface 9. Although soft-foamed plastics material is preferred for pad 3, other resilient materials may readily be substituted that will meet the structural and functional requirements of devices according to the present invention. Moreover, the illustrated square shape of pad 3 is non-essential, as is the illustrated cylindrical shape of central aperture 5.

Figure 2:
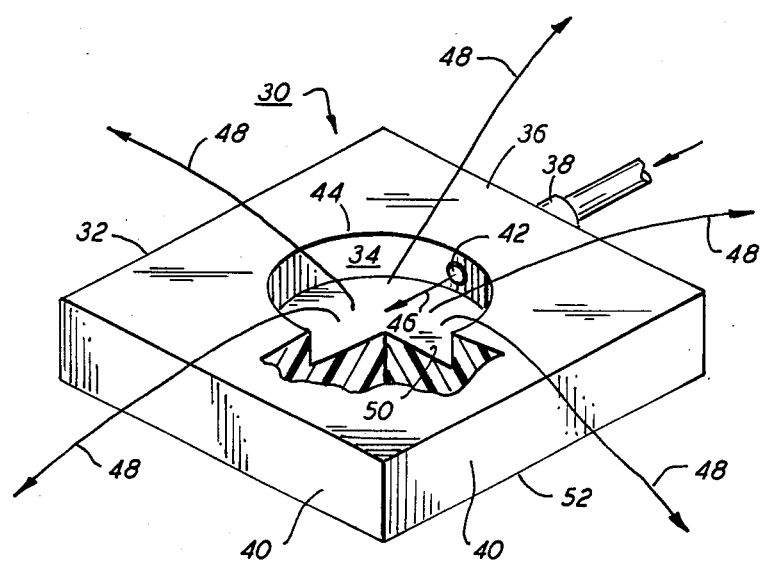
FIG. 2 is an isometric broken-out half sectional view of another hyperbaric gas treatment device in accordance with the present invention.

Referring now to FIG. 2, a hyperbaric device 30 is shown which constitutes another embodiment of the present invention and which differs from the FIG. 1 embodiment by using a gas inlet/central aperture arrangement that eliminates any need for encasing the pad. Here, a square resilient pad 32 of soft-foamed plastic material is provided with a central cylindrical aperture 34 which extends only about halfway through pad 32 from the upper major surface 36 thereof. A gas inlet fitting 38 penetrates one of the minor pad surfaces 40 and extends laterally within pad 32 along a radius of aperture 34 until its outlet end 42 emerges through the aperture sidewall.

In operation, device 30 is positioned on the patient's body by yieldably pressing upper major pad surface 36 against the skin with the mouth 44 of aperture 34 circumscribing a skin lesion. Hyperbaric oxygen, supplied from a suitable regulated source (not shown) is then continuously discharged from fitting 38 in the direction shown by the arrow 46 to impinge on the lesion. The lesion-impinging oxygen escapes past the aperture mouth 44 in paths it establishes to atmosphere between major pad surface 36 and the skin yieldably pressed thereby, such paths being suggested in FIG. 2 by the arrows 48. The escaping oxygen, as in the FIG. 1 embodiment, develops a soothing pad vibration that is imparted to the tender sensitive skin immediately surrounding the lesion.

The pad material between the bottom 50 of aperture 34 and the lower major pad surface 52 provides the function provided by transparent casing 7 (FIG. 1) to constrain the pressurized gas to escape radially outwards from the lesion. However, such pad material does not provide the visual access to the lesion that is provided by transparent casing 7. Therefore, should visual access be desired with an inlet fitting feeding directly into a central pad aperture, the FIG. 2 embodiment may be modified to use the casing of FIG. 1 to encase pad 32 and be further modified to extend central aperture 34 completely through pad 32. The FIG. 2 embodiment altered by these modifications is shown in FIG. 4 as device 30' held by a strap 54 in yieldable pressing engagement with the patient's skin, with hyperbaric oxygen being supplied to inlet fitting 38 for impingement upon the skin lesion and massage-inducing escape thereafter to atmosphere in paths 48 which are established between the patient's skin and the modified device 30'.

Figure 5:
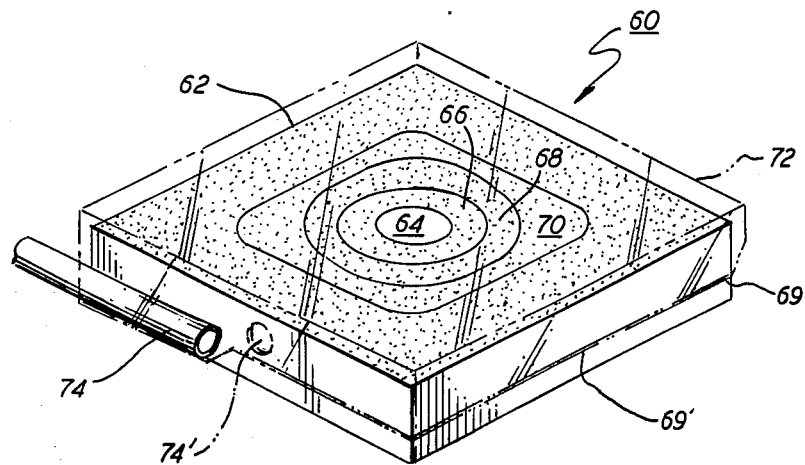
FIG. 5 is an isometric view of yet another hyperbaric gas treatment device in accordance with the present invention.

FIG. 5 shows a hyperbaric gas treatment device somewhat similar to the embodiment of FIG. 1, having a modified gas constraining membrane 72 and not yet provided with a central aperture in its resilient pad 62. The resilient pad 62 of device 60 has scored therethrough the outlines of three concentric cylindrical holes 64, 66 and 68 and a surrounding coaxial outline of a square hole 70, the common axis of holes 64–70 being normal to the parallel opposed pair of major surfaces of pad 62.

The transparent flexible sheet or membrane 72 is secured to the resilient pad 62 rather than encasing it as in FIG. 1. In the illustrated embodiment of FIG. 5, the sheet 62 is secured to the minor or side surfaces 69 by, for example, an adhesive bond on the surfaces 69 or a friction coupling in a slit 69' or both. A gas inlet fitting 74 hermetically penetrates sheet 72 at a corner and extends along one of the sides 69 of pad 62 above the line of attachment. If desired, the sheet 72 can be adhesively bonded to the top surface of the pad 62 beyond the outline of the hole 70, in which case the gas inlet fitting can be inserted into an access hole 74' penetrating helf way through the pad.

Device 60 is prepared for use by first determining which of the scored hole outlines 64–70 in pad 62 has a perimeter that will best circumscribe the skin lesion to be treated. The central core delineated by this outline is thereafter removed from pad 62 from the bottom side. The scored outlines can be precut either partially or completely through the thickness of the pad. In the latter case, the parts can be held by a transparent membrane (not shown) adhesively bonded to the bottom surface and adapted to be cut to release the selected core piece.

Figure 6:
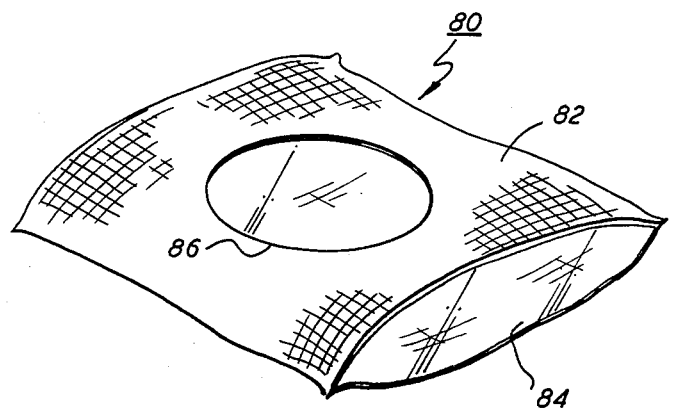
FIG. 6 is an isometric view of a disposable cover which may fit removably over any one of the hyperbaric gas treatment devices shown in FIGS. 1 to 5 while the device is applying therapy.

FIG. 6 shows a disposable cover 80 which may be removably fitted about any of the hyperbaric devices 1, 30, 30' or 60 thusfar described. Cover 80 is fashioned as a two-piece sleeve, one piece 82 being of a soft laminated fabric and the other piece 84 being of transparent flexible sheet material. The fabric piece 82 is provided with a central hole 86 for circumscribing the skin lesion to be treated. When cover 80 is slipped over the casing of an encased resilient pad, treating gas escaped from the hyperbaric device along paths between the casing and cover and between the cover and patient causes a gentle vibration of the device which is transmitted to the skin surrounding the lesion.

Figure 7:
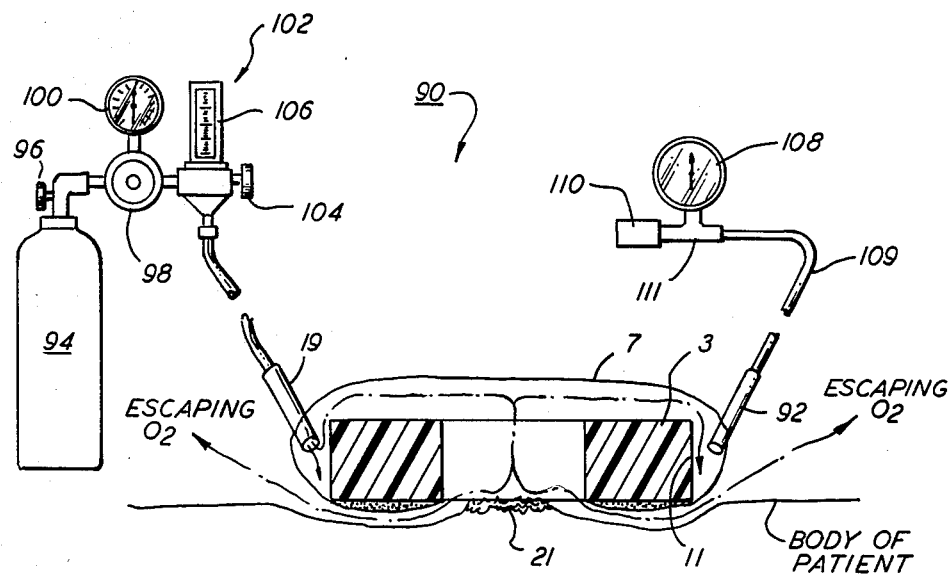
FIGS. 7 and 8 are schematic picturizations of exemplary oxygen supply and pressure measuring set-ups employed in the utilization of the invention.

FIG. 7 shows a hyperbaric gas treatment device 90 somewhat similar to device 1 depicted in FIG. 1 and, accordingly, like parts in FIGS. 1 and 7 are identified by like reference numerals. Device 90, however, is provided with a gas fitting 92 which is additional to gas inlet fitting 19 and which hermetically penetrates casing 7 near a corner of pad 3 to extend a short distance alongside that minor pad surface 11 opposite the minor pad surface alongside which gas inlet fitting 19 extends. FIG. 7 moreover illustrates an example of a suitable arrangement for supplying oxygen to device 90 in which a cylinder 94 of compressed oxygen is connected through a shut-off valve 90 to a pressure reducer 98 equipped with a pressure gauge 100. The output of reducer 98 is connected to inlet fitting 19 via a flow regulator 102 equipped with a flow rate adjustment knob 104 and a flow rate gauge 106 which indicates in liters per minute the adjusted rate of flow of oxygen through inlet fitting 19. If desired, a humidifier (not shown) may be disposed in the connection between flow regulator 102 and gas inlet fitting 19. In operation, device 80 is yieldably pressed against the body of a patient by, for example, hold-down straps (not shown) and the oxygen flow rate is adjusted to provide a hyperbaric oxygen pressure of about 22 mm Hg within device 90 and, consequently, on lesion 21. An indication of the pressure thus provided is presented by a pressure gauge 108 connected to the stem of a Tee-coupling 111, one arm of which is connected by way of tubing 108 to fitting 92, the other arm being directly connected to a pressure relief valve 110. Typically, relief valve 110 is set to open at an oxygen pressure of about 25 mm Hg in order to avert pressure interference with capillary circulation of the patient near lesion 21 undergoing treatment.

Figure 8:
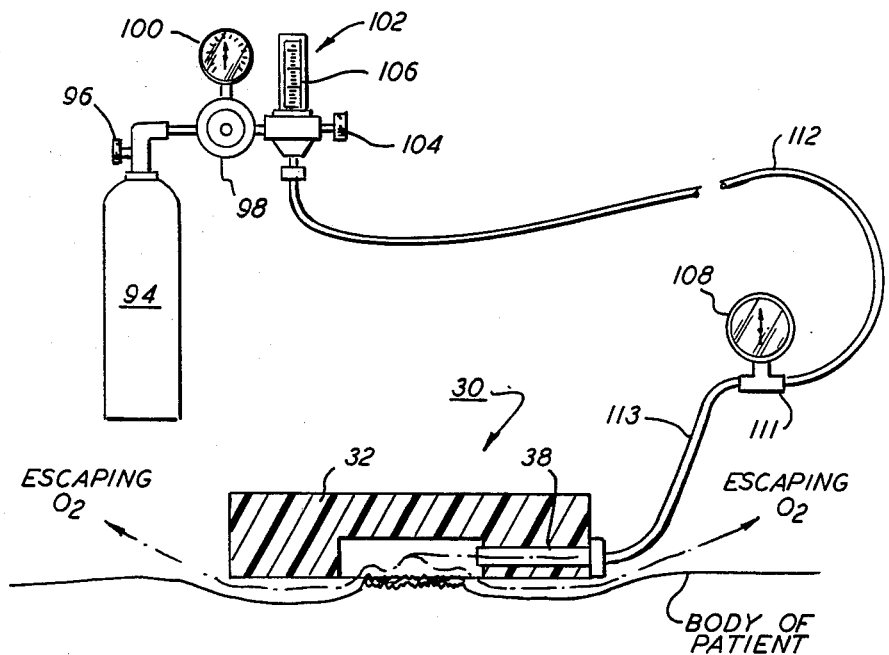

In FIG. 8, hyperbaric gas treatment device 30 of FIG. 2 is shown in an inverted operative state relative to that shown in FIG. 2. The oxygen supplying arrangement 94–106 and pressure indicating gauge 108 of FIG. 7 are again used in FIG. 8 in conjunction with device 30. However, as gas inlet fitting 38 is the sole gas fitting with which device 30 is equipped, the arm of gauge Tee-coupling 111 which was directly connected to pressure relief valve 110 in FIG. 7 is now connected instead by a tubing length 112 to flow regulator 102, whereas the other arm is connected by a tubing length 113 to fitting 38. Thus, in order to provide an indication of the oxygen pressure within device 30 while it is yieldingly pressed against the body of a patient, gauge 108 of FIG. 8 is located in the oxygen supply line comprised of tubing lengths 112, 113.

While the invention has been particularly shown and described with reference to the preferred embodiments thereof, it will be understood by those skilled in the art that various alterations in form and detail may be made therein. For example, the geometry of the pad can be varied by rounding the corners and edges and gentle embossing patterns can be included in the patient engaging surfaces to augment exhausting of gases.

We claim:

1. A hyperbaric gas treatment device for therapeutic topical treating of skin lesions, comprising:
   a resilient pad having a centrally apertured surface as a major side thereof;
   means for conducting pressurized treating gas into the central aperture of said surface; and
   means for constraining the pressurized gas flowing into said aperture to escape from said aperture only past the aperture periphery at said surface;
   said central aperture extending partially through the pad towards another major side thereof, said constraining means including the pad material disposed between the bottom of said central aperture and said other major side of said pad;
   said surface being yieldably pressable against the skin of a patient to circumscribe said aperture periphery substantially about a lesion of the skin and, upon conduction of pressurized treating gas into said aperture, to provide gas escape paths between the skin and said surface in which the escaping gas flows from said aperture periphery to atmosphere.

2. A device according to claim 1, wherein said conducting means comprises an elongated tubular member extending within said pad with an outlet end in direct communication with said central aperture and with an external inlet end adapted for connection to a source of pressurized treating gas.

3. A device according to claim 1, wherein said gas constraining pliable sheet is secured to the side edges of the pad around the entire periphery thereof.

4. A hyperbaric gas treatment device for therapeutic topical treating of skin lesions, comprising:
   a resilient pad having at least an opposing pair of major outer surfaces, at least one of which is provided with an opening extending therefrom toward the other major outer surface;
   a casing of gas-impervious flexible sheet material encasing all outer surfaces of said pad and having a single aperture therethrough, said aperture being in the casing portion which engages said one major outer surface and being in substantial registration with said opening; and
   a gas inlet fitting which penetrates said casing adjacent a peripheral portion of said pad for supplying pressurized treating gas from an external source to said opening in said pad;
   said device being adapted to be yieldably positioned against the skin of a patient with said casing aperture substantially circumscribing a skin lesion and, while so positioned and while pressurized treating gas is continuously fed via said fitting to said pad opening for impingement upon said lesion, to permit the escape of treating gas to atmosphere along paths between said device and the patient.

5. A device according to claim 4, wherein a casing cover is removably fitted about said casing and is of soft fabric at least throughout an areal portion thereof which coextensively overlies said one major outer surface of the encased path, said areal portion of said cover having an aperture therethrough substantially registering with said aperture of said casing portion.

6. A device according to claim 4 or 5, wherein said pad opening extends through the pad to said other major outer surface.

7. A device according to claim 5, wherein said gas inlet fitting extends alongside a minor outer surface of said pad intermediate said opposing pair of major outer surfaces so that its outlet is disposed between said minor outer surface and the casing portion engaging said minor outer surface and is in indirect communication with said pad opening at least by way of paths between said other major outer surface and the casing portion engaging said other major outer surface.

8. A device according to claim 5, wherein at least the casing portion which engages said other major outer surface is transparent to facilitate visually the positioning of said device with respect to said skin lesion.

9. A device according to claim 4 or 5, wherein the outlet of said gas inlet fitting is in direct communication with said pad opening at a location within said pad spaced from said one major outer surface.

10. A device according to claim 4 or 5, wherein said resilient pad is of gas-pervious material.

11. A device according to claim 4 or 5, wherein said resilient pad is of gas-impervious material.

12. A device according to claim 4 or 5, wherein said casing portion is uniformly adhered into engagement with said one major outer surface of said pad.

13. A device according to claim 4 or 5, wherein said gas inlet fitting is hermetically sealed about its periphery to said casing where it penetrates said casing.

14. A device according to claim 4 or 5, wherein said resilient pad is of soft foamed plastic.

15. A device according to claim 14 wherein the soft foamed plastic is of open-cell construction.

16. A device according to claim 14, wherein the soft foamed plastic is of closed-cell construction.

17. A device according to claim 14, wherein said resilient pad is of a rectangular configuration.

18. A device according to claim 14, wherein said opening is cylindrical.

19. A hyperbaric gas treatment device for therapeutic topical treating of skin lesions, comprising:
   a resilient pad having at least a pair of parallel major outer pad surfaces and outlines of a plurality of concentric cylindrical holes scored therethrough between said major pad surfaces, the common axis of which is normal to said parallel opposed pair of major surfaces of said pad;
   a casing of gas-impervious flexible sheet material loosely encasing all outer surfaces of said pad and adapted to be cut to form circular holes in registry with any one of said outlines; and
   treating gas inlet means hermetically penetrating said casing to communicate with the minor and major pad surfaces;
   said device being such that upon cutting a circular hole in said casing in registry with one adjacent periphery of a scored cylindrical hole outline through the pad, then removing the pad material within said scored outline to create a corresponding cylindrical hole and thereafter yieldably pressing the encased pad against the skin of a patient with the casing hole circumscribing a lesion to be treated, pressurized treating gas caused to be discharged from said inlet means will enter the cylindrical hole at the ends thereof by way of paths between said casing and the minor and major pad surfaces and escape to atmosphere by way of paths it establishes between the casing and the patient's skin.

20. A hyperbaric gas treatment device for therapeutic topical treating of skin lesions, comprising:
   - a resilient pad having at least an opposing pair of major external surfaces, at least one of which is provided with an opening extending therefrom toward the other major external surface;
   - a casing of gas-impervious flexible sheet material encasing said pad and engaging all external surfaces of said pad, the casing portion which engages said one major external surface of said pad having an aperture therethrough substantially registering with said opening in said one major external surface;
   - a casing cover removably fitted about said casing and being of soft fabric at least throughout an areal portion thereof which coextensively overlies said one major external surface of the encased pad, said areal portion of said cover having an aperture therethrough substantially registering with said aperture of said casing portion; and
   - a gas inlet fitting which penetrates said casing and which extends alongside a minor external surface of said pad intermediate said opposing pair of major external surfaces, said fitting being hermetically sealed to said casing about the periphery of said fitting;
   - said device, in use, being positioned with the aperture of said areal portion of the cover substantially circumscribing a skin lesion of a patient while pressurized treating gas is continuously fed via said fitting into said casing, thereby to maintain a reservoir of treating gas in the pad opening for contacting the lesion by way of the apertures registered with the pad opening, the excess treating gas escaping from the device along paths between the casing and cover and between the cover and patient.

* * * * *